United States Patent [19]

Shafiee et al.

[11] Patent Number: 5,352,783
[45] Date of Patent: Oct. 4, 1994

[54] MICROBIAL TRANSFORMATION PRODUCT HAVING IMMUNOSUPPRESSIVE ACTIVITY

[75] Inventors: Ali Shafiee, Westfield; Byron H. Arison, Watchung; Shieh-Shung T. Chen, Morganville; Randall R. Miller, Piscataway; Ralph A. Stearns, Park Ridge, all of N.J.

[73] Assignee: Merck & Co., Inc., Rahway, N.J.

[21] Appl. No.: 74,258

[22] Filed: Jun. 9, 1993

[51] Int. Cl.$^5$ ............... C07D 491/16; A61K 31/345; C12P 17/14
[52] U.S. Cl. ..................... 540/456; 435/119
[58] Field of Search ......................... 540/456

[56] References Cited

U.S. PATENT DOCUMENTS

| | | | |
|---|---|---|---|
| 3,244,592 | 4/1966 | Arai | 167/65 |
| 4,894,366 | 1/1990 | Okuhara et al. | 514/63 |
| 4,975,372 | 12/1990 | Arison et al. | 435/119 |
| 4,987,139 | 1/1991 | Chen et al. | 514/321 |
| 5,138,052 | 8/1992 | Chen et al. | 540/456 |

FOREIGN PATENT DOCUMENTS

| | | | |
|---|---|---|---|
| 0378317 | 7/1990 | European Pat. Off. | 540/456 |
| 0378320 | 7/1990 | European Pat. Off. | 540/456 |
| 0396400 | 11/1990 | European Pat. Off. | 540/456 |
| WO93/05058 | 3/1993 | PCT Int'l Appl. | 540/456 |
| 2245891 | 1/1992 | United Kingdom | 540/456 |

*Primary Examiner*—Robert T. Bond
*Attorney, Agent, or Firm*—J. Eric Thies; David L. Rose; Joseph F. DiPrima

[57] ABSTRACT

Microbial transformation of a macrolide immunosuppressant by the microorganism Streptomyces sp., (Merck Culture Collection MA 6960) ATCC No. 55387 yields a compound of the structural formula (I):

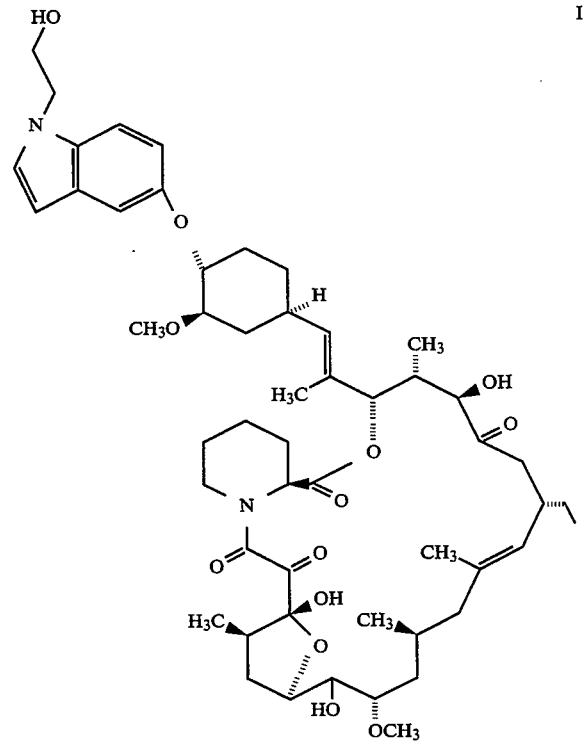

This compound is an immunosuppressant useful in a mammalian host for the treatment of autoimmune diseases, infectious diseases, the prevention of rejection of foreign organ transplants and/or related afflictions, diseases and illnesses.

1 Claim, 1 Drawing Sheet

FIG. 1

MICROBIAL TRANSFORMATION PRODUCT HAVING IMMUNOSUPPRESSIVE ACTIVITY

SUMMARY OF THE INVENTION

The present invention is directed to the novel immunosuppressant compound (I):

I

This compound may be prepared by biotransformation of the macrolide immunosuppressant which has the structural formula (II):

II

Compound (I) is useful in a mammalian host for the treatment of autoimmune diseases (such as juvenile-onset diabetes mellitus, multiple sclerosis and rheumatoid arthritis), immunodepression, infectious diseases and/or the prevention of rejection of foreign organ transplants (e.g. bone marrow and heart transplants and xeno transplants) and is also useful in the topical treatment of inflammatory and hyperproliferative skin diseases and cutaneous manifestations of immunologically-mediated illnesses (such as: psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus, Alopecia areata), male pattern alopecia, alopecia senilis, reversible obstructive airways disease, particularly asthma, alopecia, inflammation of mucosa and blood vessels, cytomegalovirus infection, multidrug resistance, idiopathic thrombocytopenic purpura, Behcet's syndrome, conjunctivitis, Crohn's disease, Mooren's ulcer, uveitis, severe intraocular inflammation, and/or hepatic injury associated with ischemia.

This invention also relates to processes for the preparation of the novel compound by fermentation of the microorganism Streptomyces sp., (Merck Culture Collection MA 6960) ATCC No. 55387 in the presence of substrate compound II.

This invention further relates to pharmaceutical compositions comprising a therapeutically effective amount of the compound (I) in combination with a pharmaceutically acceptable nontoxic carrier or excipient.

In addition, this invention relates to a method for the treatment of and the prevention of certain afflictions, diseases and illnesses.

BRIEF DESCRIPTION OF DISCLOSURES IN THE ART

Fujisawa United States, European and Japanese patents and applications (U.S. Pat. No. 4,894,366, issued Jan. 16, 1990, EPO Publication No. 0,184,162 and PBJ Disclosure 63-17884) and publications (*J. Am. Chem. Soc.*, 1987, 109, 5031 and *J. Antibiotics* 1987, 40, 1249) disclose 17-allyl-1,14-dihydroxy-12-[2'-(4'-hydroxy-3''-methoxycyclohexyl)-1'-methylvinyl]-23,25-dimethoxy-13,19,21,27-tetra-methyl-11,28-dioxa- 4-azatri-cyclo-[22.3.1.0^4,9]octacos-18-ene-2,3,10,16-tetraone (FR-900506), (FK-506), (L-679,934), 17-ethyl-1,14-di-hydroxy-12-[2'-(4''-hydroxy-3''-methoxycyclohexyl)- 1'-ethylvinyl]-23,25-dimethoxy-13,19,21,27-tetramethyl-11,28-dioxa-4-azatricyclo[22.3.1.0^4,9]octacos-18-ene-2,3,10,16-tetraone (FR-900520) and related compounds. The macrolide FR-900506 is produced by fermentation of a particular strain of *Streptomyces tsukubaensis*. The macrolide FR-900520 is produced by *S. hydroscopicus* subsp. *yakushimaensis*. The synthetic preparation of FR-900506 has recently been reported (*J. Am. Chem. Soc.*, 1989, 111, 1157). A Sandoz European patent application (EPO Publication No. 0,356,399) discloses stereoisomers of FR-900506 and derivatives at the 17-position. Fisons European and WIPO patent applications (EPO Publication No. 0,323,04.2 and PCT Publication No. WO 89/05304) disclose various derivatives of FR-900506, FR-900520 and related compounds. A Sandoz European Patent application (EPO Publication No. 0,437,680) discloses chloro, bromo, iodo and azido derivatives of FR-900506, FR-900520 and related compounds. A Merck European Patent application (EPO Publication No. 0.428.365) discloses various amino derivatives of FR-900506, FR-900520 and related compounds. A Fujisawa patent application (UK Publication No. GB 2,245,891-A) discloses various derivatives of FR-900506 bearing a heterocyclic group. U.S. Pat. No. 3,244,592 to T. Arai describes the culturing of *Streptomyces hygroscopicus* var. *ascomyceticus* to produce the antifungal "ascomycin."

Fujisawa United States patents (U.S. Pat. No. 4,929,611, issued May 29, 1990, U.S. Pat. No. 4,956,352, issued Sep. 11, 1990 and U.S. Pat. No. 5,110,811, issued May 5, 1992) disclose FK-506-type compounds as being useful in treating resistance to organ transplantation. A Sandoz European patent application (EPO Publication No. 0,315,978) discloses the use of FR-900506 and related compounds in the topical treatment of inflammatory and hyperproliferative skin diseases and of cutaneous manifestations of immunologically-mediated illness. A Fisons WIPO patent application (PCT Publication No. WO 91/04025) discloses the use of various derivatives of FR-900506 in the treatment of immunodepression. A Fisons WIPO patent application (PCT Publication WO 90/14826) discloses the use of FR-900506 and related compounds in the treatment of reversible obstructive airways disease, particularly asthma. A Fujisawa European patent application (EPO Publication No. 0,423,714) discloses the use of FK-506 and derivatives as hair revitalizing agents. Various studies have suggested the efficacy of FK-506 in the treatment of a number of ailments, including rheumatoid arthritis (C. Arita, et al., *Clincial exp. Immunol.* 1990, 82, 456–461; N. Inamura, et al., *Clin. Immunol. Immunopathol.* 1988, 46, 82–90), recent-onset diabetes (N. Murase, et al., *Diabetes*, 1990, 39, 1584–86; N. Murase, et al., *Lancet*, 1990, 336, 373–74), posterior uveitis (H. Kawashima, *Invest. Ophthalmol. Vis. Sci.*, 1988, 29, 1265–71), hepatic injury associated with ischemia (M. Sakr, et al., *Life Sci.*, 1990, 47,687–91) allergic encephalomyelitis (K, Deguchi, et al., *Brain Nerve*, 1990, 42, 391–97), glomerulonephritis (J. McCauley, et al., *Lancet*, 1990, 335, 674) and systemic lupus erythematosus (K. Takabayashi, et al., *Clin, Immunol. Immunopathol.*, 1989, 51, 110–117) multidrug resistance (M. Naito, et al., *Cancer Chemother. Pharmacol.*, 1992, 29, 195–200), inflammation of mucosa and blood vessels (PCT Publication WO 91/17754), cytomegalovirus infection (UK Publication GB 2,247,620A), and idiopathic thrombocytophenic purpura and Basedow's disease (PCT Publication WO 91/19495).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was approved by the US FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, tacrolimus, FR-900506, FK-506, (17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]-octacos-18-ene-2,3,10,16-tetraone) and related compounds which were isolated and characterized by Tanaka, Kuroda, and co-workers at Fujisawa Pharmaceutical Co. in Japan, see *J. Am. Chem. Soc.*, 1987, 109, 5031, and U.S. Pat. No. 4,894,366, issued Jan. 16, 1990) have been shown to possess exceptional immunosuppressive activity. Fujisawa United States patents (U.S. Pat. No. 4,929,611, issued May 29, 1990, U.S. Pat. No. 4,956,352, issued Sep. 11, 1990 and U.S. Pat. No. 5,110,811, issued May 5, 1992) disclose the use of FK-506-type compounds in treating resistance to organ transplantation in patients. In particular, the compound FR-90506 has been reported to be 100 times more effective than cyclosporin in the suppression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), male pattern alopecia or alopecia senilis (EPO Publication No. 0,423,714), rheumatoid arthritis (C. Arita, et al., *Clincial exp. Immunol.*, 1990, 82, 456–461; N. Inamura, et al., *Clin. Immunol, Immunolpathol.* 1988, 46, 82–90), recent-onset diabetes (N. Murase, et al., *Diabetes,* 1990, 39, 1584–86; N. Murase, et al., *Lancet,* 1990, 336, 373–74), posterior uveitis (H. Kawashima, *Invest. Ophthalmol. Vis. Sci.,* 1988, 29, 1265–71 ), hepatic injury associated with ischemia (M. Sakr, et al., *Life Sci.,* 1990, 47, 687–91 ) allergic encephalomyelitis (K, Deguchi, et al., *Brain Nerve,* 1990, 42, 391–97), glomerulo-nephritis (J. McCauley, et al., *Lancet,* 1990, 335,674), systemic lupus erythematosus (K. Takabayashi, et al., *Clin. Immunol, Immunopathol.,* 1989, 51, 110–117) multidrug resistance (M. Naito, et al., *Cancer Chemother. Pharmacol.,* 1992, 29, 195–200), inflammation of mucosa and blood vessels (PCT Publication WO 92/17754), cytomegalovirus infection (UK Publication GB 2,247,620A), and idiopathic thrombocytophenic purpura and Basedow's disease (PCT Publication WO 91/19495).

DETAILED DESCRIPTION OF THE INVENTION

The compound (I) of this invention is:

I or a pharmaceutically acceptable salt thereof.

The compound of the present invention is prepared by fermentation of the microorganism Streptomyces sp. (MA 6960) ATCC No. 55387 in the presence of the substrate compound (II)

II under submerged aerobic conditions at an appropriate temperature in an aqueous carbohydrate medium comprising assimilable sources of nitrogen and carbon and isolation of the resulting biotransformation products, compounds (I) in a conventional manner. The fermentation is conducted at a pH of about 7 for a sufficient time to selectively monodemethylate compound (II) (i.e. remove the methyl group from the C-13 methoxyl group) and cause a rearrangement of the six-membered pyranyl ring to a five-membered furanyl ring with the freeing of the hydroxyl group at C-14.

A biologically pure sample of the microorganism Streptomyces sp. MA 6960 is currently on restricted deposit in the permanent culture collection of the American Type Culture Collection, 12301 Parklawn Drive in Rockville, Md., with Accession Number ATCC 55387.

On the basis of the taxonomic analysis performed thus far, the microorganism MA 6960 has tentatively been assigned in the order Streptomyces. Further taxonomic characteristics are being examined to place this organism conclusively within a genus and species.

The following is a general description of Streptomyces sp. strain MA6960 (CIBE isolate 9027-53, ATCC 55387) Observations of growth, general cultural characteristics and carbon source utilization were made in accordance with the methods of Shirling and Gottleib (Internat. J. System. Bacteriol. 16:313–340). Chemical composition of the cells was determined using the methods of Lechevalier and Lechevalier (in Actinomycete Taxonomy, A. Dietz and D. W. Thayer, Ed. Society for Industrial Microbiology, 1980). Whole cell fatty acids were derivatized and analyzed as methyl esters (FAMEs) by gas chromatography by the procedure of Miller and Berger using a MIDI is Microbial Identification System (Microbial Identification Systems, Newark, Del.). Coloration of the culture was determined by comparison with color standards contained in the Inter-Society Color Council-National Bureau of Standards Centroid Color Charts (US Dept. of Commerce National Bureau of Standards supplement to NBS Circular 553, 1985).

Analysis of Cell Wall Composition—Peptidoglycan contains LL-diaminopimelic acid.

General growth characteristics—Good growth on yeast malt extract agar (YME), glycerol asparagine agar, inorganic salt starch agar, oatmeal, trypticase soy agar, Czapek's agar, and peptone iron agar. Fair growth on tap water agar supplemented with 0.02% NZ-amine A (Shefield Chemical Co.) Culture also grows in tryptone yeast extract broth. Culture grows at 27° C. and 37° C.

Colony morphology—(on YME at 21 d) Substrate mycelium is orange-yellow. Aerial mycelium light gray with black and white patches. Spore mass is abundant and light light gray in color. Colonies are opaque, raised and have entire edges, rubbery in consistency with a rough surface texture.

Micromorphology—Aerial roycelia (0.57 μm) arise from substrate roycelia and are branched. In mature cultures (7–28d p.i.) the aerial mycelium terminates in chains of spores that are in extended spirals. On occasion, pseudoverticils are obsevered and coelescence of the aerial spore mass occurs on inorganic salts starch agar. This characteristic is especially noticeable in areas of dense aerial development. Sporulation occurs on YME, inorganic salts-starch agar, oatmeal, glycerol asparagine agar, tap water agar with NZ-amine and Czapek's agar.

Miscellaneous physiological reactions—Culture does not produce $H_2S$ in peptone-iron agar and neither melanoid nor other soluble pigments were osevered in any of the media tested. Starch is weakly hydrolyzed. Carbon source utilization pattern is as follows: good utilization of L-arabinose, D-fructose, α-D-glucose, inositol, α-D-lactose, β-D-lactose, D-maltose, D-mannitol, D-mannose, D-raffinose, sucrose, D-xylose; moderate utilization of D-arabinose, no utilization of L-rhamnose.

Cellular Fatty Acid Analysis—Gas chromatography of FAMEs, prepared from cultures grown on trypticase-soy broth agar (BBL) for 4d at 27° C. revealed that the major fatty acids ($\geq 5\%$ total fatty acid content) of this strain are: $16:0_{iso}$ (29%), $15:0_{anteiso}$ (13%), $15:0_{iso}$ (12%), $14:0_{iso}$ (12%) and $16:1_{iso}$ H (8%).

Diagnosis—Cell wall analysis reveals that MA6960 has a type I cell wall. Morphological studies reveal that the culture produces long chains of spores on spiral sporophores. Sporophores arise from the aerial mycelium. These are characteristics typical for strains of the genus Streptomyces. A comparison of the phenotypic data of MA6960 with that of the validly published species of Streptomyces in the taxonomic literature (Shirling, E. B. and Gottlieb, D., Int. J. System. Bacteriol. 18: 69 (1968); Shirling, E. B. and Gottlieb, D., Int. J, System. Bacteriol. 18: 279 (1968); Shirling, E. B. and Gottlieb, D., Int. J, System. Bacteriol. 19: 391 (1969); Shirling, E. B.. and Gottlieb, D., Int. J. System. Bacteriol. 22: 265 (1972); Nonomura, H. J. Ferment. Technol. 52: 78 (1974); Pridham, T. and Tresner, H., in Bergey's Manual of Determinative Bacteriology, Eight Edition, R. E. Buchanan and N. E. Gibbons, Ed., Williams and Wilkins, Baltimore (1974); and Loci, R. in Bergey's Manual of Systematic Bacteriology, Vol 4., St. Williams, M. E. Sharpe and J. G. Holt. Ed., Williams and Wilkins, Baltimore. (1989)) shows that this strain bears a resemblance to Streptomyces lidicus, Streptomyces rimosus, Streptomyces rocheii and Streptomyces violaceusniger. Of these four species, only Stmy lidicus and Stmy violaceusniger are reported to exhibit coelescence of the aerial spore mass and neither are know to exhibit the pseudoverticil arrangement exhibited by MA6960. In addition, neither of these species are reported to utilize arabinose. Comparison of the fatty acid profiles against the MIDI actinomycete library (Version 3.7) showed a distant match to *Stmy lidicus.* Based on these data, it is believed that MA6960 is novel strain of *Streptomyces lydicus.*

| Cultural characteristics of Streptomyces sp. MA6960 at 21 days ||||| 
|---|---|---|---|---|
| Medium | Amount of Growth | Aerial Mycelium and/or Spores | Soluble Pigments | Reverse Color |
| Yeast Extract Malt Extract | good | Aerial mycelium light gray (264 l.Gray) with black and white patches. Spores borne in extended spirals on pseudoverticils. | none noted | Light orange yellow (701 OY) |
| Glucose Asparagine | good | Aerial mycelium light gray (264 l.Gray) with black and white patches. Spores borne in extended spirals, some on pseudoverticils. | none noted | Pale yellow (89pY) |
| Inorganic Salts Starch | good | Aerial mycelium light gray (264 l.Gray) with black and white patches. Spores borne in extended spirals on pseudoverticils. Coelescent spore mass. Starch weakly hydrolyzed | none noted | Pale yellow (89pY) |
| Oatmeal | good | Aerial mycelium light gray (264 l.Gray). Spores borne on short extended spirals. | none noted | Pale yellow (89pY) |
| Tap Water | moderate | Aerial mycelium light gray (264 l.Gray) with black and white patches. Spores borne in short spirals on pseudoverticils. | none noted | Transparent |
| Czapek | good | White (263 White) Poorly developed aerial growth, no spores observed. | none noted | Pale yellow (89pY) |
| Peptone Iron | good | | Melanin negative, H$_2$S negative | |

| Carbohydrate utilization pattern of Streptomyces sp. MA6960 at 21 days ||
|---|---|
| Carbon source | Utilization |
| D-arabinose | 2 |
| L-arabinose | 3 |
| D-fructose | 3 |
| inositol | 3 |
| α-D-lactose | 3 |
| β-D-lactose | 3 |
| D-maltose | 3 |
| D-mannitol | 3 |
| D-mannose | 3 |
| D-raffinose | 3 |
| L-rhamnose | 0 |
| sucrose | 3 |
| D-xylose | 3 |
| a-D-glucose (control) | 3 |

3 = good utilization
2 = moderate utilization
1 = poor utilization
0 = no utilization The present invention process can be practiced with any strain of Streptomyces sp. capable of producing compound (I), and particularly preferred is the ATCC No. 55387 strain.

In general, compound (I) may be produced by culturing (fermenting) the above described microorganism in the presence of an appropriate concentration of substrate compound (II) in an aqueous nutrient medium containing sources of assimilable carbon and nitrogen, preferably under submerged aerobic conditions (e.g. shaking culture, submerged culture, etc.). An appropriate concentration of the parent compound in the aqueous medium ranges from 0.01 mg/ml to 0.5 mg/ml, preferably 0.05 mg/ml. The aqueous medium is incubated at a temperature between 26° C. and 29° C., preferably 27° C. The aqueous medium is incubated for a period of time necessary to complete the oxidative biotransformation as monitored by HPLC, usually for a period of about 24–48 hours, on a rotary shaker operating at about 220 rpm with a throw of about 2 in. The aqueous medium is maintained at a pH between 6 and 8, preferably about 7, at the initiation and termination (harvest) of the fermentation process. A higher or lower pH will cause the culture to die. A higher pH also leads to a substantial and/or total loss of product. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described herein below.

The preferred sources of carbon in the nutrient medium are certain carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids, and the like.

The carbon and nitrogen sources, though advantageously employed in combination, need not be used in their pure form because less pure materials which contain traces of growth factors and considerable quantities of mineral nutrients are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

Substrate compound (II) can be obtained by synthetic organic procedures hereinafter described.

Submerged aerobic cultural conditions may be preferred for the production of compound (I) in massive amounts. For the production in small amounts, a shaking or surface culture in a flask or bottle is employed.

Furthermore, when the growth is carried out in large tanks, it is preferable to use the vegetative form of the organism for inoculation in the production tanks in order to avoid growth lag in the process of production of compound (I).

Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of compound (I) and is generally autoclaved to sterilize the medium prior to inoculation. The fermentation medium is generally adjusted to a pH between 6 and 8, preferably about 7, prior to the autoclaving step by suitable addition of an acid or base, preferably in the form of a buffering solution.

Agitation and aeration of the culture mixture may be accomplished in a variety of ways. Agitation may be provided by a propeller or similar mechanical agitation equipment, by revolving or shaking the fermentor, by various pumping equipment or by the passage. of sterile air through the medium. Aeration may be effected by passing sterile air through the fermentation mixture.

The fermentation is usually conducted at a temperature between about 20° C. and 40° C., preferably 25°-35° C., for a period of about 10 hours to 20 hours, which may be varied according to fermentation conditions and scales. Preferably, the production cultures are incubated for about 17 hours at 27° C. on a rotary shaker operating at 220 rpm, wherein the pH of the fermentation medium is maintained at 7.0 to harvest.

Preferred culturing/production media for carrying out the fermentation include the following media:

|  | g/l |
| --- | --- |
| KE Seed Medium | |
| Dextrose | 1.0 |
| Dextrin | 10.0 |
| Beef Extract | 3.0 |
| Ardamine pH | 5.0 |
| NZ Amine Type E | 5.0 |
| $MgSO_4.7H_2O$ | 0.05 |
| $K_2HPO_4$ | 0.37 |
| Adjust pH to 7.1 | |
| Add $CaCO_3$ | 0.5 g/l |
| Biotransformation Medium | |
| Glucose | 20.0 |
| Soya Meal | 5.0 |
| Yeast Extract | 5.0 |
| NaCl | 5.0 |
| MES | 9.8 |
| Adjust pH to 7.0 | |

The biotransformation product, compound (I), may be recovered from the culture medium by conventional means which are commonly used for the recovery of other known biologically active substances. Compound (I) is found in the cultured mycelium and filtrate, which are obtained by filtering or centrifuging the cultured broth, and accordingly can be isolated and purified from the mycelium and the filtrate by a conventional method such as concentration under reduced pressure, lyophilization, extraction with a conventional solvent, such as methanol and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred recovery method is solvent extraction, particularly using methanol. A preferred purification method involves the use of chromatography, especially HPLC, using a silica gel count and an eluant mixture composed of water and an organic solvent such as methanol, acetonitrile and the like. A preferred eluant is composed of water and acetonitrile and is run through the column in a linear gradient. The compound obtained according to the fermentation processes as explained above can be isolated and purified in a conventional manner, for example, extraction, precipitation, fractional crystallization, recrystallization, chromatography, and the like.

Compound (I) exhibits immunosuppressive activity, i.e., positive inhibition of T-cell activation, as demonstrated by the calcium ionophore (ionomycin) plus phorbol myristate acetate (PMA) induced T-cell stimulation assay, also referred to herein as the "T-cell proliferation assay". The principle of this assay is to measure the proliferation of mouse T lymphocytes stimulated with the combination of ionomycin plus PMA. A positive sample in this assay will inhibit T-ell proliferation, as indicated by reduced tritiated thyroidinc uptake.

The compounds of the present invention are capable of forming salts with various inorganic and organic acids and bases and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, pierate, pivalate, propionate, succinate, tartrate, tosylate, and undecanoate. Base salts include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The compounds of Formula I may be employed as an immunosuppressant or antimicrobial compound by methods and in dosages known in the prior art for other macrolide immunosuppressants. The compound possesses pharmacological activity such as immunosuppressive activity, antimicrobial activity, and the like, and therefore is useful for the treatment and prevention of the resistance to transplantation or transplantation rejection of organs or tissues (such as heart, kidney, liver, lung, bone marrow, cornea, pancreas, intestinum tenue, limb, muscle, nervus, medulla ossium, duodenum, small-bowel, medulla ossium, skin, pancreatic islet-cell, etc. including xeno transplantation), graft-versus-host diseases by medulla ossium transplantation, autoimmune diseases such as rheumatoid arthritis, systemic lupus erythematosis, nephrotic syndrome lupus, Hashimoto's thyroiditis, multiple sclerosis, myasthenia gravis, type I diabetes mellitus, type H adult onset diabetes, uveitis, nephrotic syndrome, steroid-dependent and steroid-resistant nephrosis, Palmo-planter pustulosis, allergic encephalomyelitis, glomerulonephritis, etc., and infectious diseases caused by pathogenic microorganisms.

The compound of Formula I is also useful for treating inflammatory, proliferative and hyperproliferative skin diseases and cutaneous manifestations of immunologically-mediated illnesses such as: psoriasis, psoriatic arthritis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, acne, Alopecia areata, eosinophilic fasciitis, and atherosclerosis. More particularly, the compound of Formula I is useful in hair revitalizing, such as in the treatment of male or female pattern alopecia or alopecia senilis, by providing epilation prevention, hair germination, and/or a promotion of hair generation and hair growth.

The compound of Formula I is further useful in the treatment of respiratory diseases, for example sarcoidosis, fibroid lung, idiopathic interstitial pneumonia, and reversible obstructive airways disease, including conditions such as asthma, including bronchial asthma, allergic asthma, intrinsic asthma, extrinsic asthma and dust asthma, particularly chronic or inveterate asthma (for example late asthma and airway hyper-responsiveness), bronchitis and the like.

The compound of Formula I is also be useful for treating hepatic injury associated with ischemia.

The compound of the invention is also indicated in certain eye diseases such as keratoconjunctivitis, vernal conjunctivitis, uveitis associated with Behcet's disease, keratitis, herpetic keratitis, conical cornea, dystorphia epithelialis corneae, corneal leukoma, ocular pemphigus, Mooren's ulcer, Scleritis, Graves's ophthalmopathy, severe intraocular inflammation, and the like.

The compound of Formula I is useful for treating multidrug resistance of tumor cells, (i.e. enhancing the activity and/or sensitivity of chemotherapeutic agents), preventing or treating inflammation of mucosa or blood vessels (such as leukotriene $B_4$mediated diseases, gastric ulcers, vascular damage caused by ischemic diseases and thrombosis, ischemic bowel disease, inflammatory bowel disease (e.g., Crohn's disease and ulcerative colitis) nercotizing enterocolitis), or intestinal lesions associated with thermal burns,. cytomegalovirus infection, particularly HCMV infection.

Further, the compound of Formula I is also useful for treating or preventing renal diseases including interstitial nephritis, Goodpasture's syndrome, hemolytic-uremic syndrome and diabetic nephropathy; nervous diseases selected from multiple myositis, Guillain-Barre syndrome, Meniere's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung and idiopathic interstitial pneumonia; skin diseases including dennatomyositis, leukoderma vulgaris, ichthyosis vulgaris, photoallergic sensitivity and cutaneous T cell lymphoma; circulatory diseases including arteriosclerosis, aortitis syndrome, polyarteritis nodosa and myocardosis; collagen including scleroderma, Wegener's granuloma and Sjogren's syndrome; adiposis; eosinophilic fasciitis; periodontal disease; nephrotic syndrome; hemolytic-uremic syndrome; and muscular dystrophy.

Further, the compound of the invention is indicated in the treatment of diseases including intestinal inflammations/allergies such as Coeliac disease, proctitis, eosinophilic gastroenteritis, mastocytosis, Crohn's disease and ulcerative colitis; and food related allergic diseases which have symptomatic manifestation remote from the gastrointestinal tract, for example migraine, rhinitis and eczema.

The compound of the invention also has liver regenerating activity and/or activity in stimulating hypertrophy and hyperplasia of hepatocytes. Therefore, they are useful for the treatment and prevention of hepatic diseases such as immunogenic diseases (e.g. chronic autoimmune liver diseases including autoimmune hepatitis, primary billary cirrhosis and sclerosing cholangitis), partial liver resection, acute liver necrosis (e.g. necrosis caused by toxins, viral hepatitis, shock or anoxia), B-virus hepatitis, non-A/non-B hepatitis and cirrhosis.

The compound of the invention is also indicated for use as antimicrobial agents, and thus may be used in the treatment of diseases caused by pathogenic microorganisms and the like.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semi-solid, or liquid form, and in addition auxiliary, stabilizing, thickening and coloring agents and perfumes may be used.

The tablets, pills, capsules, troches and the like may also contain the following ingredients: a binder such as micro-crystalline cellulose, gum tragacanth or gelatin; an excipient such as starch or lactose, a disintergrating agent such as alginic acid, Primogel, cornstarch and the like a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating compounds, sucrose as a sweetening agent and certain preservatives, dyes, coloring and flavors. Materials used in preparing these various compositions should be pharmaceutically pure and non-toxic in the amounts used.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, cirates or phosphates and agents for the adjustment of tonicity such as sodium chloride or dextrose. The parenteral preparation can be enclosed in disposable syringes or multiple dose vials made of glass or plastic.

For example, the compound of Formula I may be utilized with hydroxypropyl methylcellulose essentially as described in U.S Pat. No. 4,916,138, issued Apr. 10, 1990, or with a surfactant essentially as described in EPO Publication 0,428,169. Oral dosage forms may be prepared essentially as described by T. Hondo, et al., *Transplantation Proceedings.* 1987, XIX, Supp. 6, 17–22. Dosage forms for external application may be prepared essentially as described in EPO Publication 0,423,714. The active object compound is included in the pharmaceutical composition in an amount sufficient to produce the desired effect upon the process or condition of diseases.

For the treatment of these conditions and diseases caused by inunmunoirregularity the compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of reversible obstructive airways disease, it is preferable that the compound of Formula I be administered by inhalation to the lung, especially in the form of a powder.

The compound of Formula I may optionally be employed in co-therapy with anti-proliferative agents. Particularly preferred is co-therapy with an antiproliferative agent selected from the group consisting of: azathioprine, brequinar sodium, deoxyspergualin, mizaribine, mycophenolic acid morpholino ester, cyclosporin. and rapamycin.

Dosage levels of the compound of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 mg per patient per day, assuming a 70 kg patient). In addition, the compound of the present invention may be administered on an intermittent basis; i.e. at daily, semi-weekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally comprise from about 0.01 mg to about 500 mg, and preferably about 0.5 mg to about 100 mg of active ingredient. For external administration the compound of Formula I may be formulated within the range of, for example, 0.0001% to 60% by weight, preferably from 0.001 to 10% by weight, and most preferably from about 0.005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

7-Ethyl-1,14-dihydroxy-12-[2'-(4"-(1-hydroxyethyl-indol-5-yl)oxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene2,3,10,16-tetraone (Compound II)

STEP 1A 1-(2-Hydroxyethyl)-5-bromoindole

A mixture of NaOH (4.4 gm, 0.011 tool) in DMSO (175 ml) was stirred at 100° C. for 5 hours at which time it was cooled to 20° C. To this mixture was added 5-bromoindole (20 gm, 0.102 mol) and the reaction was stirred for 8 hours at room temperature. A solution of ethylene oxide (5.1 gm, 0.125 mol) in DMSO (20 ml) was prepared by bubbling the gas into DMSO. To the bromoindole reaction mixture was slowly added the ethylene oxide solution and stirring was continued for another 2.5 hours. The reaction mixture was then poured into ice water and extracted twice with diethyl ether. The combined ether extracts were concentrated in vacuo whereupon crystallization took place. The crude product was recrystallized from diethyl ether:-hexanes (3:2) to afford the title compound (6.25 gm).

STEP 1B 1-(2-t-Butyldimethylsilyloxyethyl)-5-bromoindole

A solution of 1(2-hydroxyethyl)-5-bromoindole (6 gm, 0.025 mol), t-butyldimethylsilyl chloride (4.5 gm, 0.03 mol) and triethylamine (4.2 ml, 0.03 mol) in $CH_2Cl_2$ (60 ml) was stirred for 12 hours at room temperature. The reaction mixture was then washed twice with $H_2O$, dried over $Na_2SO_4$, filtered and concentrated in vacuo to provide the title compound as a yellow oil. $^1H$ NMR was consistent with the desired structure.

STEP 1C

Tri[1-(2-t-butyldimethylsilyloxyethyl)-indol-5-yl]-bismuthine

To a solution of 1(2-t-butyldimethylsilyloxyethyl)-5bromoindole (1.4 gm, 0.004 mol) in diethyl ether (14 ml) at −78° C. was added t-butyl lithium (4.7 ml of a 1.7M solution in pentanes, 0.008 mol). After stirring for 1.5 hours, a solution of bismuth trichloride (0.4 gm, 0.013 mol) in THF (4 mL) was added. The reaction was stirred at −78° C. for 2 hours and then allowed to warm slowly to room temperature and stirring was continued a further 8 hours. The reaction mixture was then poured into H₂O and extracted with toluene. The combined organic extracts were dried over Na₂SO₄, filtered and the flitrate was concentred in vacuo. Purification by chromatography (silica, 4:1, hexanes:ethyl acetate) provided the title compound (1.03 gm) as a semisolid. $^1$H NMR was consistent with desired structure.

STEP 1D

17-Ethyl-1,14-dihydroxy-12--[2'-(4''-(1-t-butyldimethylsilyloxyethylindol-5-yl)oxy-3''-methoxycyclo-hexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a solution of tri[1-(2-t-butyldimethyl-silyloxyethyl)-indol-5-yl]bismuthine (1.03 gm, 0.001 mol) in CH₂Cl₂ (10 ml) at room temperature was added peracetic acid (150 μL). After stirring for 15 minutes, 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (1 gm) was added to the reaction mixture followed by Cu-(OAc)₂ (0.04 gm) and the reacton mixture was stirred for 20 hours. To the reaction mixture was then added saturated NaHCO₃ and it was then extracted with CH₂Cl₂. The organic extracts were dried over Na₂SO₄, filtered and the fillrate was concentrated in vacuo. The crude product was purified by chromatography (silica, 3:1, hexanes:ethyl acetate) to provide the title compound (0.38 gm). $^1$H NMR was consistent with desired structure.

STEP 1E

17-Ethyl-1,14-dihydroxy-12-[2'-(4''-(1-hydroxyethyl-indol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-(1-t-butyldimethylsilyloxyethylindol-5-yl)oxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (0.38 gm) in CH₂Cl₂ (10 ml) at room temperature was added a solution of paratoluene sulfonic acid (0.05 gm) in CH₃OH (10 ml). The reaction mixture was stirred for 3 hours until TLC (silica, 2:1, hexanes:ethyl acetate) verified that reaction was complete. The reaction mixture was poured into saturated NaHCO₃ and extracted twice with CH₂Cl₂. The combined organic extracts were dried over Na₂SO₄, filtered and concentrated in vacuo. The crude product was purified by chromatography (silica, 2:1 hexanes:ethyl acetate) to provide the title compound 0.245 gm. MASS (FAB) M+Li 957. Partial $^1$H NMR (CDCl₃, 200 MHz) δ:7.18 (d, J=10 Hz, 1H); 7.16 (bs, 1H); 7.06 (d, J=4 Hz, 1H); 6.86 (dd, J=3 Hz and 10 Hz, 1H); 6.33 (d, J=4 Hz, 1H); 4.13 (t, J=6.7 Hz, 2H); 3.83 (t, J=6.7 Hz, 2H); 3.43 (s, 3H).

EXAMPLE 2

Microorganism and Culture Conditions

A frozen vial (2.0 ml) of culture (MA6960) ATCC No. 55387 was used to inoculate a 250 ml baffled shake flask containing 50 ml of an autoclaved (sterilized) KE seed medium consisting of (in units of grams/liter) dextrin 10.0. dextrose 1.0, beef extract 3.0, Ardamine PH (Yeast Products, Inc.) 5.0, N-Z Amine type E 5.0, MgSO₄.7H₂O 0.05, K₂HPO₄ 0.37, and CaCO₃ 0.5. The pH of the seed medium was adjusted to 7.1 before autoclaving. The seed was incubated in the seed medium at 27° C. for 20 hours on a rotary shaker operating at 220 rpm. A 2.5 ml aliquot of the resulting seed medium was used to inoculate a 250 ml Eriemeyer shake flask containing 50 ml of the following previously autoclaved (sterilized) soy-glucose medium[1]. A solution of the substrate compound (II) was added to the fermentation at zero time of incubation at 27° C. to achieve a final concentration of 0.05 mg/ml. The shake flask contents were subsequently incubated overnight at 25° C. on a rotary shaker operating at 220 rpm.

1. Soy-glucose medium consisted of (in units of grams/liter) glucose 20.0; Soya meal 5.0; yeast extract 5.0; NaCl 5.0; MES 5.0 where the pH was adjusted to 7.0 before autoclaving.

Isolation and Purification of the Biotransfonnation Product (Compound I)

Ten flasks containing biotransfonnation broth were pooled (250 ml) and extracted three times with 20 ml dichloromethane. (The aqueous phase did not contain any microbial transformation products when tested by HPLC.) The dichloromethane extract was dried over sodium sulfate and evaporated to dryness under reduced pressure. The resulting oil was dissolved in acetonitrile and subjected to high performance liquid chromatography (HPLC) purification.

HPLC was carried out on Whatman Magnum 9 Partisil 10 ODS-3 at 60° C. and monitored at 205 run. The column was developed at 3 ml/min with a linear gradient from 55% acetonitrile in 0.1% aqueous phosphoric acid to 85% acetonitrile in 0.1% aqueous phosphoric acid in 30 minutes. The parent compound eluted at 30.03 minutes. The desired compound was collected during repeated injections of the above described extract. The fractions at a retention time of 20.24 minutes were pooled, concentrated and extracted with dichloromethane. The dichloromethane extract was dried over sodium sulfate and evaporated to dryness to yield 300 mg of the compound (I).

EXAMPLE 3

Characterization of Biotransformation Products

Figure 1:
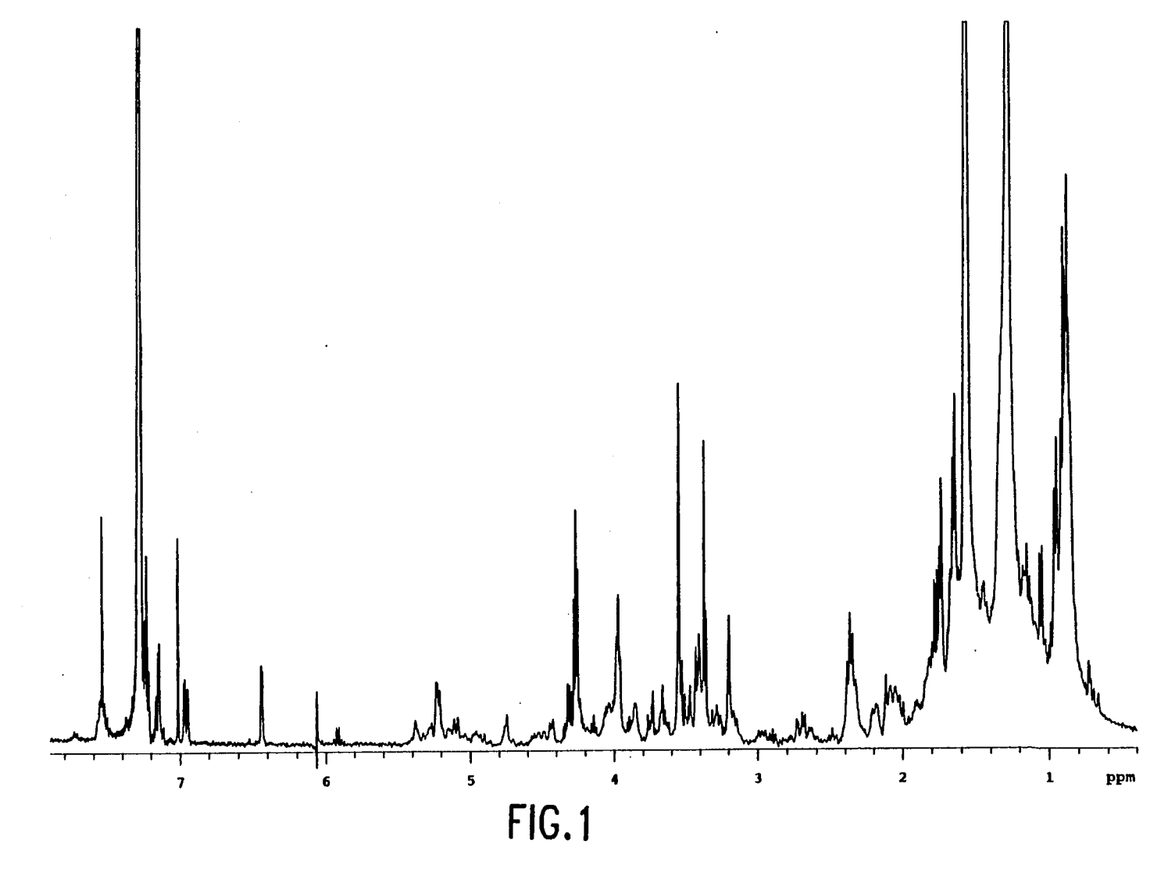
FIG. 1 is a proton nuclear magnetic resonance (NMR) spectrum taken at 400 MHz of Compound I in $CD_3OD$.

Compound (I) of this invention was identified via NMR spectroscopy (CD₃OD, 400 MHz) yielding the proton NMR spectrum depicted in FIG. 1.

Compound (I) was further identified by Mass spectroscopy as follows:

Mass spectra were obtained by LC/MS/MS (ionspray) on a SCIEX API III tandem mass spectrometer. The mobile phase consisted of 40% CH₃CN/0.05% TFA in 10 mm ammonium acetate. Ionization was effected by pneumatically assisted electrospray (ion spray). The starting material gave an ammonium adduct ion (M+NH₄)⁺=969 and the biotransfonnation product gave primarily (M+NH₄)⁺=955, corresponding to a nominal mass of 937 Da, a loss of 14 Da from the starting material. The daughter ion spectrum of the ammonium adduct ion (collision gas: argon; 70 eV) is presented below in tabular form:

| Mass | Relative Intensity |
| --- | --- |
| 370 | 22% |
| 532 | 11 |
| 550 | 100 |
| 955 | 21 |

The loss of 14 Da from the starting material suggested that the biotransformation product was a demethylated derivative. Comparison of the respective daughter ion spectra showed that the major fragment ion had changed from m/z 564 for the starting material to m/z 550 for the biotranformation product. This fragment is believed to result from scission of the C-1-0 and C-24,25 bonds (numbering from FK-506 structure), indicating the demethylation of either the C-13 or C-15 methoxy group.

EXAMPLE 4

T-Cell Proliferation Assay

The immunosuppressive inhibitory activity of compound (I) was determined as follows:

1. Sample Preparation

The compound to be assayed was dissolved in absolute ethanol at 1 mg/ml.

2. Assay

Spleens from C57B 1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool colunms were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The colunms were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$ M 2-mercaptoethanol and 50 µg/ml gentamycin. Ionomycin was added at 250 ng/ml and PMA at 10 ng/ml. The cell suspension was immediately distributed into 96 well flat-bottom microculture plates (Costar) at 200 µl/well. The various dilutions of the compound to be tested were then added in triplicate wells at 20 µl/well. The compound 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-aza-tricyclo[22.3.1.0$^{4,9}$]octacos-18-ene-2,3,10,16-tetraone was used as a standard. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 µCi/well of tritiated thymidine (NEN, Cambridge, MA). After another 4 hours of incubation, cultures were harvested on glass fiber filters using a multiple sample harvester. Radioactivity of filter discs corresponding to individual wells was measured by standard liquid scintillation counting methods (Betacounter). Mean counts per minute of replicate wells were calculated and the results expressed as concentration of compound required to inhibit tritiated thymidine uptake of T-cells by 50%.

Compound I was tested according to the previous procedure and had activity in inhibiting the proliferation of T-cells in the aforementioned assay.

The results of this assay are representative of the intrinsic immunosuppressive activity of the compound of the present invention.

For determining antagonist activity, the foregoing procedure is modified in that dilutions of compounds are cultured with 17-ally-1,14-dihydroxy-12-[2'-(4"-hydroxy-3"-methoxycyclohexyl)-1'-methyl-vinyl]-23,25-dimethoxy-13,19,21,27-tetramethyl-11,28-dioxa-4-azatricyclo[22.3.1.0$^{4,9}$]octacos-18-ene-2,3,10,-16-tetraone (as a standard) at a concentration of 1.2 nM, a concentration which inhibits T cell proliferation by 100%, the concentration of compound required to reverse the inhibition obtained by the standard alone by 50% is measured, and the $ED_{50}$ value is determined.

While the foregoing specification teaches the principles of the present invention. with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of formula I:

or a pharmaceutically acceptable salt thereof.

* * * * *